(12) United States Patent
Jono et al.

(10) Patent No.: US 7,754,923 B2
(45) Date of Patent: Jul. 13, 2010

(54) METHOD FOR PRODUCING NITROGEN-CONTAINING COMPOUND

(75) Inventors: Masaharu Jono, Wakayama (JP); Michio Terasaka, Wakayama (JP); Hideki Taniguchi, Wakayama (JP); Tetusaki Fukushima, Wakayama (JP)

(73) Assignee: KAO Corporation, Tokyo (JP)

( * ) Notice: Subject to any disclaimer, the term of this patent is extended or adjusted under 35 U.S.C. 154(b) by 3 days.

(21) Appl. No.: 12/224,607

(22) PCT Filed: Mar. 8, 2007

(86) PCT No.: PCT/JP2007/054504

§ 371 (c)(1),
(2), (4) Date: Sep. 2, 2008

(87) PCT Pub. No.: WO2007/102568

PCT Pub. Date: Sep. 13, 2007

(65) Prior Publication Data

US 2009/0054688 A1     Feb. 26, 2009

(30) Foreign Application Priority Data

Mar. 8, 2006     (JP)     ............... 2006-062452

(51) Int. Cl.
*C07C 209/78* (2006.01)
*C07C 291/04* (2006.01)

(52) U.S. Cl. .................... 564/488; 564/298

(58) Field of Classification Search ........ None
See application file for complete search history.

(56) References Cited

U.S. PATENT DOCUMENTS

| | | | |
|---|---|---|---|
| 4,448,998 A | 5/1984 | King | |
| 4,937,384 A | 6/1990 | Dobson | |
| 5,075,505 A | 12/1991 | Forquy et al. | |

FOREIGN PATENT DOCUMENTS

| | | | |
|---|---|---|---|
| DE | 1493839 | | 3/1970 |
| JP | 63-255253 | A | 10/1988 |
| JP | 8-245524 | A | 9/1996 |
| JP | 9-241222 | A | 9/1997 |
| JP | 10-168052 | A | 6/1998 |
| JP | 2001-302596 | A | 10/2001 |
| JP | 2003-81932 | A | 3/2003 |

*Primary Examiner*—Brian J Davis
(74) *Attorney, Agent, or Firm*—Birch, Stewart, Kolasch & Birch, LLP

(57) ABSTRACT

The present invention provides a process for producing high-purity aliphatic tertiary amines containing a less amount of by-products by subjecting aliphatic acid amides to hydrogenation reduction under moderate conditions, as well as a process for producing amine derivatives from the aliphatic tertiary amines, with a good productivity in an economically advantageous manner. The present invention relates to a process for producing an aliphatic tertiary amine by subjecting a specific aliphatic amide to hydrogenation reduction in the presence of a catalyst containing copper and at least one element selected from the group consisting of elements belonging to Groups 2, 3 and 7 of the Periodic Table; the catalyst; and a process for producing amine oxide by reacting the tertiary amide obtained by the above production process with hydrogen peroxide.

10 Claims, No Drawings

METHOD FOR PRODUCING NITROGEN-CONTAINING COMPOUND

TECHNICAL FIELD

The present invention relates to a process for producing nitrogen-containing compounds, and more particularly to processes for producing aliphatic tertiary amines and amine derivatives.

BACKGROUND ART

Aliphatic tertiary amines are important intermediate products in domestic and industrial application fields, and have been used in extensive applications such as, for example, fabric softeners, antistatic agents, additives for gasoline, shampoos, rinses, bactericides and detergents.

As the method for producing the aliphatic tertiary amines, there is known an amide reduction method in which an amide obtained from inexpensive regenerative fatty acids is used as a raw material. As the amide reduction method, there are conventionally known various methods using a cobalt-based catalyst, a noble metal-based catalyst, etc. However, any of these conventional methods inevitably require to use a solvent, resulting in problems such as poor productivity.

Also, Patent Document 1 discloses the method using a copper/chromium catalyst. In addition, in Patent Document 2, it has been attempted to enhance a dehydration efficiency and improve a reactivity by physically adding zeolite to a copper/chromium catalyst. Patent Document 3 discloses the method of enhancing a durability of a copper/chromium-based catalyst by adding manganese thereto. Further, Patent Document 4 discloses a chromium-free copper-based catalyst such as a copper/zinc catalyst, a copper/zinc/ruthenium catalyst and a copper/nickel/ruthenium catalyst.

Patent Document 1: DE 1493839A
Patent Document 2: U.S. Pat. No. 4,448,998
Patent Document 3: U.S. Pat. No. 5,075,505
Patent Document 4: JP 2001-302596A

DISCLOSURE OF THE INVENTION

Problem to be Solved by the Invention

However, the methods described in the above respective Patent Documents tend to suffer from any of the problems including high reaction pressure, large load of facilities, poor reaction selectivity, etc. The present invention provides a process for producing high-purity aliphatic tertiary amines containing a less amount of by-products by subjecting aliphatic acid amides to hydrogenation reduction under moderate conditions, and a process for producing amine derivatives such as amine oxide from the aliphatic tertiary amines, with a good productivity in an economically advantageous manner, as well as catalysts used for production of the tertiary amines.

Means for Solving Problem

Thus, the present invention relates to the following aspects (1) to (3).

(1) A process for producing a tertiary amine represented by the following general formula (2):

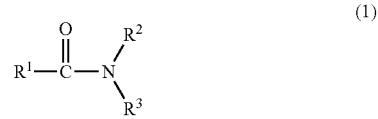

wherein $R^1$ is a linear or branched, saturated or unsaturated aliphatic hydrocarbon group having 1 to 23 carbon atoms; and $R^2$ and $R^3$ are each independently a linear or branched alkyl group having 1 to 6 carbon atoms, said process including the step of subjecting an amide represented by the following general formula (1):

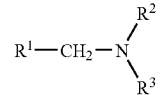

wherein $R^1$, $R^2$ and $R^3$ are the same as defined above, to hydrogenation reduction in the presence of a catalyst containing copper and at least one element selected from the group consisting of elements belonging to Groups 2, 3 and 7 of the Periodic Table (long form of the periodic table);

(2) the catalyst as defined in the above aspect (1) which is used in the process as defined in the above aspect (1); and (3) a process for producing an amine oxide, including the step of reacting the tertiary amine obtained by the process as defined in the above aspect (1) with hydrogen peroxide.

Effect of the Invention

In accordance with the present invention, a high-purity aliphatic tertiary amine containing a less amount of by-products can be produced by subjecting an aliphatic acid amide to hydrogenation reduction under moderate conditions, and amine derivatives such as amine oxide which have an excellent storage stability can be produced from the aliphatic tertiary amine, with a good productivity in an economically advantageous manner.

BEST MODE FOR CARRYING OUT THE INVENTION

The present inventors have found that the above technical tasks can be achieved by using a catalyst containing copper and at least one element selected from the group consisting of elements belonging to Groups 2, 3 and 7 of the Periodic Table.

In the process for producing a tertiary amine according to the present invention, the tertiary amine represented by the following general formula (2):

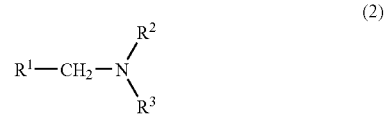

is produced by subjecting an amide represented by the following general formula (1):

to hydrogenation reduction in the presence of the catalyst.

In each of the above general formulae (1) and (2), $R^1$ represents a linear or branched, saturated or unsaturated aliphatic hydrocarbon group having 1 to 23 carbon atoms. Meanwhile, the branched saturated or unsaturated aliphatic hydrocarbon group also includes an alicyclic group. $R^1$ is preferably a linear or branched alkyl group or alkenyl group having 7 to 23 carbon atoms from the viewpoint of usefulness of the resultant tertiary amine. Examples of the alkyl or alkenyl group as $R^1$ include various heptyl groups, various octyl groups, various nonyl groups, various decyl groups, various undecyl groups, various dodecyl groups, various tridecyl groups, various tetradecyl groups, various pentadecyl groups, various hexadecyl groups, various heptadecyl groups, various octadecyl groups, various nonadecyl groups, various eicosanyl groups, various heneicosanyl groups, various tricosanyl groups, various heptenyl groups, various octenyl groups, various nonenyl groups, various decenyl groups, various undecenyl groups, various dodecenyl groups, various tridecenyl groups, various tetradecenyl groups, various pentadecenyl groups, various hexadecenyl groups, various heptadecenyl groups, various octadecenyl groups, various nonadecenyl groups, various icosenyl groups, various heneicosenyl groups and various behenyl groups. Among these groups, preferred are various heptyl groups, various nonyl groups, various undecyl groups, various tridecyl groups, various pentadecyl groups, various heptadecyl groups, various nonadecyl groups, various heneicosanyl groups, various heptenyl groups, various nonenyl groups, various undecenyl groups, various tridecenyl groups, various pentadecenyl groups, various heptadecenyl groups, various nonadecenyl groups and various heneicosenyl groups. The term "various" used herein means all of those groups having a linear chain or a branched chain.

In each of the above general formulae (1) and (2), $R^2$ and $R^3$ are each independently a linear or branched alkyl group having 1 to 6 carbon atoms. Meanwhile, the "branched alkyl group" also includes a cycloalkyl group. Examples of $R^2$ and $R^3$ respectively include methyl, ethyl, n-propyl, isopropyl, n-butyl, isobutyl, sec-butyl, tert-butyl, various pentyl groups, various hexyl groups, cyclopentyl and cyclohexyl. Among these alkyl groups, preferred are methyl, ethyl and propyl from the viewpoint of usefulness of the resultant tertiary amine. $R^2$ and $R^3$ may be the same or different.

Examples of the amide represented by the above general formula (1) include N,N-dimethyl aliphatic acid amides such as N,N-dimethyl caprylamide, N,N-dimethyl 2-ethylhexane amide, N,N-dimethyl caprinamide, N,N-dimethyl lauroyl amide, N,N-dimethyl myristoyl amide, N,N-dimethyl palmitoyl amide, N,N-dimethyl stearoyl amide, N,N-dimethyl isostearoyl amide, N,N-dimethyl oleyl amide and N,N-dimethyl behenyl amide; and compounds obtained by replacing the N,N-dimethyl group of these aliphatic acid amides with N,N-diethyl, N,N-dipropyl, N-ethyl-N-methyl, N-methyl-N-propyl or N-ethyl-N-propyl.

On the other hand, examples of the tertiary amine represented by the above general formula (2) include amine compounds corresponding to the above exemplified amide compounds of the general formula (1). Specific examples of the tertiary amine include N,N-dimethyl aliphatic amines such as N,N-dimethyl octyl amine, N,N-dimethyl 2-ethylhexyl amine, N,N-dimethyl decyl amine, N,N-dimethyl lauryl amine, N,N-dimethyl myristyl amine, N,N-dimethyl hexadecyl amine, N,N-dimethyl stearyl amine, N,N-dimethyl isostearyl amine, N,N-dimethyl oleyl amine and N,N-dimethyl behenyl amine; and compounds obtained by replacing the N,N-dimethyl group of these aliphatic amines with N,N-diethyl, N,N-dipropyl, N-methyl-N-propyl, N-ethyl-N-methyl, N-methyl-N-propyl or N-ethyl-N-propyl.

The catalyst used in the present invention contains (a) copper and (b) at least one element selected from the group consisting of elements belonging to Groups 2, 3 and 7 of the Periodic Table (long form of the periodic table), and preferably contains, in addition to the components (a) and (b), (c) at least one element selected from the group consisting of elements belonging to Groups 8 to 10 of the Periodic Table.

The at least one element selected from the group consisting of elements belonging to Groups 2, 3 and 7 of the Periodic Table as the component (b) is preferably at least one element selected from the group consisting of calcium, barium, manganese and lanthanum from the viewpoints of good activity and selectivity of the resultant catalyst. In addition, the at least one element selected from the group consisting of elements belonging to Groups 8 to 10 of the Periodic Table as the component (c) which may be used in the preferred catalyst is preferably at least one element selected from the group consisting of platinum-group elements, more specifically, ruthenium, rhodium, palladium, osmium, iridium and platinum. Among these platinum-group elements, more preferred is at least one element selected from the group consisting of ruthenium, rhodium and palladium.

Examples of preferred configurations of the catalyst include Cu/Ca-based catalysts, Cu/Ba-based catalysts, Cu/Mn-based catalysts, Cu/Mn/Ru-based catalysts, Cu/La/Ru-based catalysts and Cu/La/Pd-based catalysts.

In the catalyst used in the present invention, the mass ratio of the component (b) to the component (a) [(b)/(a)] is preferably from 0.05 to 10 and more preferably from 0.05 to 5 from the viewpoint of a good activity of the resultant catalyst. Further, the mass ratio of the component (c) to the component (a) [(c)/(a)] is preferably from 0.0001 to 0.1 and more preferably from 0.0005 to 0.05 from the viewpoint of a good activity of the resultant catalyst.

In the present invention, by using such a composite metal-based catalyst, a high economical catalytic performance which has never been expected from those catalysts made of a single metal substance can be achieved.

The contents of the respective metal elements except for platinum-group elements may be quantitatively determined using a wavelength dispersive fluorescent X-ray analyzer. More specifically, 5 g of lithium tetraborate and a stripping agent ($LiCO_3$:LiBr:$LiNO_3$=5:1:5) are added to 0.1 g of a sample containing the respective metal elements, and the resultant mixture is fused with an alkali at 1050° C. to prepare glass beads thereof. The thus prepared glass beads are evaluated using a wavelength dispersive fluorescent X-ray analyzer "ZSX100e" available from Rigaku Corporation. The thus measured X-ray intensity values of the respective metal elements in the sample are compared with those in a calibration curve prepared by mixing high-purity samples of the respective metal elements at aimed concentrations, thereby determining the contents of the respective metal element in the sample.

On the other hand, the contents of the platinum-group elements in the catalyst is determined as follows. That is, 0.5 g of a sample is charged together with ammonium hydrogensulfate in an amount several ten times the amount of the sample, into a testing tube made of a hard glass, and decomposed under heating. Then, the resultant decomposed product is dissolved in water under heating, and the obtained solution is subjected to ICP emission spectrometry to measure the contents of the platinum-group elements in the solution.

In the catalyst used in the present invention, the composite metals may be supported on a carrier. Examples of the carrier include silica, alumina, silica-alumina, zirconia, activated carbon, zeolite and diatomaceous earth, though not particularly limited thereto. These carriers may be used singly or in combination of any two or more thereof. The method of supporting the catalyst on the carrier is not particularly limited, and may be appropriately selected from conventionally known methods such as an impregnation method, a precipitation method and an ion-exchange method depending upon kind of the carrier used. The amount of the catalyst supported on the carrier is preferably from 5 to 70% by mass and more preferably from 10 to 60% by mass in terms of metal oxide on the basis of the carrier.

The catalyst used in the present invention may be produced, for example, by the following method.

That is, an aqueous solution containing nitrates, sulfates, chlorides, etc., of the respective metal elements is mixed with an alkali agent such as sodium hydroxide and sodium carbonate and further optionally with a carrier to prepare a precipitate, and the thus prepared precipitate is subjected to solid-liquid separation by a suitable method such as filtration and centrifugal separation. Next, the obtained solid is washed with ion-exchanged water, dried and then calcined preferably at a temperature of from about 300 to about 1000° C., thereby producing the aimed catalyst in the form of a metal oxide.

In the process for producing the tertiary amine according to the present invention, the amide represented by the above general formula (1) is subjected to hydrogenation reduction in the presence of the thus produced catalyst.

The hydrogenation reduction may be carried out in a hydrogen atmosphere under normal pressures or under a hydrogen-applied pressure, or in a flowing hydrogen under normal pressures or under applied pressure. The reaction may be conducted by either a continuous method or a batch method. In the batch method, the amount of the catalyst added is usually from about 0.05 to about 20% by mass and preferably from 0.1 to 10% by mass on the basis of the raw amide from the viewpoints of a good reactivity, suppression of production of by-products and low production costs. The reaction temperature is usually from about 140 to about 300° C. and preferably from 160 to 270° C. from the viewpoints of enhancing the reaction rate and suppressing production of by-products. The reaction pressure is usually from normal pressures to about 25 MPa, preferably from 0.1 to 5.0 MPa and more preferably from 0.1 to 3.0 MPa from the viewpoints of enhancing the reaction rate and suppressing increase in load of facilities.

Thus, when subjecting the amide represented by the general formula (1) to hydrogenation reduction under the moderate conditions, the tertiary amine represented by the general formula (2) which contains a less amount of by-products and has a high purity can be produced with a good productivity in an economically advantageous manner.

The present invention also provides a catalyst for production of tertiary amines which can be used in the above process for producing the tertiary amine according to the present invention. The details of the catalyst are the same as described previously.

In the present invention, there is also provided a process for producing amine derivatives by using the tertiary amine produced according to the above production process, in particular, a process for producing amine oxide.

In the process for producing amine oxide, the tertiary amine obtained by the above production process is used as a raw material and reacted with hydrogen peroxide.

In the present invention, as the hydrogen peroxide to be reacted with the tertiary amine, there may be used industrially available aqueous solutions containing hydrogen peroxide in an amount of from 20 to 90% by mass. Although any of the aqueous solutions containing hydrogen peroxide within the above-specified concentration range may be used in the present invention, the concentration of hydrogen peroxide in the aqueous solutions is preferably 35 by mass from the viewpoint of a good safety and a good availability. The amount of hydrogen peroxide used is preferably from 0.9 to 1.2 mol, more preferably from 0.95 to 1.1 mol and still more preferably from 1.0 to 1.05 mol per 1 mol of the tertiary amine from the viewpoint of suppressing residual unreacted amine.

The temperature used upon the reaction between the tertiary amine and hydrogen peroxide is preferably from 20 to 100° C., more preferably from 30 to 95° C. and still more preferably from 40 to 90° C. from the viewpoint of suppressing decomposition of hydrogen peroxide. The reaction between the tertiary amine and hydrogen peroxide may be conducted in the presence of a known catalyst to promote the reaction. Examples of the catalyst used in the above reaction include carbon dioxide; a mixture of sodium bicarbonate and sodium pyrophosphate; citric acid, tartaric acid and salts thereof; and phosphotungstic acid and salts thereof.

Further, the reaction between the tertiary amine and hydrogen peroxide may be conducted in a solvent. Water may be usually used as the solvent. However, in order to well control the viscosity of the aqueous amine oxide solution, water may also be used in combination with a water-soluble solvent such as methanol, ethanol and isopropanol.

In the process for producing the tertiary amine according to the present invention, it is possible to produce the tertiary amine with a high reactivity. Further, by using the thus produced tertiary amine as a raw material, it is possible to produce amine oxide therefrom at low production costs. Thus, the tertiary amine produced by the process of the present invention is suitably used for producing amine derivatives such as amine oxide. The amine oxide has been used as an auxiliary activator for various detergents, for example, suitably used in extensive applications such as cleaning agents for tableware, shampoos and detergents for clothes.

Examples of the amine derivatives other than amine oxide which are produced from the tertiary amine obtained according to the present invention include benzalkonium chloride, alkyl trimethyl ammonium salts and alkyl dimethyl ammonia acetic acid salts. These compounds may be produced by any suitable known methods.

EXAMPLES

The present invention is described in more detail by referring to the following examples, etc. However, it should be noted that these examples, etc., are only illustrative and not intended to limit the invention thereto.

Production Example 1

A separable flask was charged with 100 g of copper nitrate trihydrate and 39 g of calcium nitrate tetrahydrate. The contents of the flask were dissolved in 2000 mL of water, and then heated while stirring. The flask was further charged with 31 g of synthesized zeolite ("ZEOLUM F-9" available from Tosoh Corporation) at 50° C., and then 584 g of a 10 mass % Na$_2$CO$_3$ aqueous solution (content of Na$_2$CO$_3$: equimolar amount based on the metal salts) was dropped to the above obtained solution at 90° C. over 1 h. The resultant mixed solution was further stirred for 1 h. Thereafter, the resultant precipitate was subjected to filtration and washing with water, and further dried at 110° C. over a whole day and night. The obtained dried product was calcined at 600° C. in air for 1 h, thereby obtaining a copper-based catalyst. As a result, it was confirmed that the mass ratio of copper to calcium (Cu:Ca) in the metal oxides contained in the thus obtained copper-based catalyst was 4:1, and the amount of the catalyst supported on the carrier (proportion of copper oxide to a sum of copper oxide and the carrier) was 50% by mass.

Production Examples 2 and 3

The same procedure as in Production Example 1 was repeated except for using barium nitrate or manganese nitrate in place of calcium nitrate, thereby respectively obtaining a copper-based catalyst having the mass ratio between the metal elements as shown in Table 1.

Production Examples 4 and 5

The same procedure as in Production Example 2 was repeated except for using alumina ("MGA" available from Mizusawa Industrial Chemicals, Ltd.) or a zirconia powder ("RC-100" available from Daiichi Kigenso Kagaku Kogyo Co., Ltd.) in place of the synthesized zeolite, thereby respectively obtaining a copper-based catalyst having the mass ratio between the metal elements as shown in Table 1.

Production Example 6

A separable flask was charged with 100 g of copper nitrate trihydrate, 34 g of manganese nitrate hexahydrate and 0.54 g of ruthenium chloride. The contents of the flask were dissolved in 2000 mL of water, and then heated while stirring. The flask was further charged with 31 g of synthesized zeolite ("ZEOLUM F-9" available from Tosoh Corporation) at 50° C., and then 549 g of a 10 mass % Na$_2$CO$_3$ aqueous solution (content of Na$_2$CO$_3$: equimolar amount based on the metal salts) was dropped to the above obtained solution at 90° C. over 1 h. The resultant mixed solution was further stirred for 1 h. Thereafter, the resultant precipitate was subjected to filtration and washing with water, and further dried at 110° C. over a whole day and night. The obtained dried product was calcined at 500° C. in air for 1 h, thereby obtaining a copper-based catalyst. As a result, it was confirmed that the mass ratio between copper, manganese and ruthenium (Cu:Mn:Ru) in the metal oxides contained in the thus obtained copper-based catalyst was 4:1:0.01, and the amount of the catalyst supported on the carrier (proportion of copper oxide to a sum of copper oxide and the carrier) was 50% by mass.

Production Examples 7 and 8

The same procedure as in Production Example 6 was repeated except for using 20 g of lanthanum nitrate hexahydrate in place of 34 g of manganese nitrate hexahydrate in Production Example 7, and changing the amount of manganese nitrate hexahydrate from 34 g to 17 g and using 0.44 g of palladium chloride in place of 0.54 g of ruthenium chloride in Production Example 8, thereby respectively obtaining a copper-based catalyst having the mass ratio between the metal elements as shown in Table 1.

Comparative Production Example 1

The same procedure as in Production Example 1 was repeated except for using 100 g of copper nitrate trihydrate and 30 g of zinc nitrate in place of 100 g of copper nitrate trihydrate and 39 g of calcium nitrate tetrahydrate, thereby obtaining a Cu/Zn catalyst having the mass ratio between the metal elements as shown in Table 1.

Comparative Production Example 2

The same procedure as in Production Example 6 was repeated except for using 34 g of nickel nitrate in place of 34 g of manganese nitrate hexahydrate, thereby obtaining a Cu/Ni/Ru catalyst having the mass ratio between the metal elements as shown in Table 1.

TABLE 1

|  | Metals | Ratio between metals (mass ratio) | Carrier |
| --- | --- | --- | --- |
| Production Example 1 | Cu—Ca | 4:1 | Zeolite |
| Production Example 2 | Cu—Ba | 4:1 | Zeolite |
| Production Example 3 | Cu—Mn | 4:1 | Zeolite |
| Production Example 4 | Cu—Ba | 5:2 | Alumina |
| Production Example 5 | Cu—Ba | 4:0.5 | Zirconia |
| Production Example 6 | Cu—Mn—Ru | 4:1:0.01 | Zeolite |
| Production Example 7 | Cu—La—Ru | 4:1:0.01 | Zeolite |
| Production Example 8 | Cu—Mn—Pd | 4:0.5:0.01 | Zeolite |
| Comparative Production Example 1 | Cu—Zn | 4:1 | Zeolite |
| Comparative Production Example 2 | Cu—Ni—Ru | 4:1:0.01 | Zeolite |

Example 1

A rotary autoclave was charged with 300 g of N,N-dimethyl lauroyl amide and 5% by mass of the catalyst produced in Production Example 1 (on the basis of the raw amide). An inside of the autoclave was purged with nitrogen, and then hydrogen was introduced thereinto until an inside pressure of the autoclave was increased to 0.5 MPa. Thereafter, while maintaining the inside pressure of the autoclave at 0.5 MPa, hydrogen was introduced into the reaction system at a rate of 40 L/h (1.35 mol/h per 1 mol of the raw amide). Next, the reaction system was heated to 250° C. at which the respective components were reacted with each other, and the reaction product was sampled when the amount of the raw amide was reduced to 1%. The thus sampled reaction product was subjected to filtration to remove the catalyst therefrom, and then the composition of the thus separated reaction solution was analyzed by gas chromatography. The composition of the final reaction product is shown in Table 2.

Examples 2 to 8 and Comparative Examples 1 and 2

The same procedure as in Example 1 was repeated except for using 5% by mass (on the basis of the raw amide) of the respective catalysts as shown in Table 2 in place of 5% by mass (on the basis of the raw amide) of the catalyst obtained in Production Example 1 upon conducting the reaction. The compositions of the respective final reaction products are shown in Table 2.

TABLE 2

| | Catalyst | Composition of reaction product (mass %) | | | |
|---|---|---|---|---|---|
| | | Dimethyl lauryl amine | Dilauryl monomethyl amine | Lauryl alcohol | others |
| Example 1 | Production Example 1 | 83.5 | 6.8 | 7.6 | 2.1 |
| Example 2 | Production Example 2 | 84.9 | 5.2 | 8.3 | 1.6 |
| Example 3 | Production Example 3 | 82.1 | 7.1 | 8.6 | 2.2 |
| Example 4 | Production Example 4 | 85.6 | 4.9 | 7.1 | 2.4 |
| Example 5 | Production Example 5 | 84.5 | 5.9 | 7.9 | 1.7 |

TABLE 2-continued

| | Catalyst | Composition of reaction product (mass %) | | | |
|---|---|---|---|---|---|
| | | Dimethyl lauryl amine | Dilauryl monomethyl amine | Lauryl alcohol | others |
| Example 6 | Production Example 6 | 78.6 | 11.6 | 5.7 | 4.1 |
| Example 7 | Production Example 7 | 79.8 | 12.7 | 4.1 | 3.4 |
| Example 8 | Production Example 8 | 76.5 | 14.3 | 4.6 | 4.6 |
| Comparative Example 1 | Comparative Production Example 1 | 67.1 | 21.2 | 5.8 | 5.9 |
| Comparative Example 2 | Comparative Production Example 2 | 58.2 | 32.8 | 0.7 | 8.3 |

Example 9

A rotary autoclave was charged with 300 g of N,N-dimethyl lauroyl amide and 5% by mass of the catalyst produced in Production Example 1 (on the basis of the raw amide). While maintaining the reaction pressure at 5 MPa, hydrogen was introduced into the reaction system at a rate of 40 L/h (1.35 mol/h per 1 mol of the raw amide). Next, the respective components were reacted with each other at a temperature as shown in Table 3, and the reaction product was sampled when the amount of the raw amide was reduced to 1%. The thus sampled reaction product was subjected to filtration to remove the catalyst therefrom, and then the composition of the thus separated reaction solution was analyzed by gas chromatography. The composition of the final reaction product is shown in Table 3.

Examples 10 to 12 and Comparative Example 3

The same procedure as in Example 9 was repeated except for using 5% by mass (on the basis of the raw amide) of the respective catalysts as shown in Table 3 in place of 5% by mass (on the basis of the raw amide) of the catalyst obtained in Production Example 1 upon conducting the reaction. The compositions of the respective final reaction products are shown in Table 3.

TABLE 3

| | Catalyst | Reaction temperature (°C.) | Composition of reaction product (mass %) | | | |
|---|---|---|---|---|---|---|
| | | | DMLA*1 | DLMA*2 | LA*3 | others |
| Example 9 | Production Example 1 | 230 | 82.9 | 5.2 | 10.8 | 1.1 |
| | | 250 | 83.2 | 9.4 | 3.7 | 3.7 |
| Example 10 | Production Example 3 | 230 | 82.1 | 4.6 | 12.2 | 1.1 |
| | | 250 | 82.6 | 10.1 | 3.3 | 4.0 |
| Example 11 | Production Example 5 | 230 | 84.4 | 3.6 | 11.1 | 0.9 |
| | | 250 | 86.4 | 4.8 | 5.6 | 3.2 |
| Example 12 | Production Example 7 | 230 | 77.3 | 8.9 | 12.5 | 1.3 |
| | | 250 | 81.1 | 13.5 | 3.1 | 2.3 |
| Comparative Example 3 | Comparative Production Example 1 | 230 | 65.9 | 11.8 | 18.9 | 3.4 |
| | | 250 | 65.1 | 18.4 | 8.8 | 7.7 |

Note
*1DMLA = Dimethyl lauryl amine;
*2DLMA = Dilauryl monomethyl amine; ;
*3LA = Lauryl alcohol

Example 13

A rotary autoclave was charged with 300 g of N,N-dimethyl lauroyl amide and 5% by mass of the catalyst produced in Production Example 2 (on the basis of the raw amide). While maintaining the respective reaction pressures as shown in Table 4, hydrogen was introduced into the reaction system at a rate of 40 L/h (1.35 mol/h per 1 mol of the raw amide). Next, the respective components were reacted with each other at 250° C., and the reaction product was sampled when the amount of the raw amide was reduced to 1%. The thus sampled reaction product was subjected to filtration to remove the catalyst therefrom, and then the composition of the thus separated reaction solution was analyzed by gas chromatography. The composition of the final reaction product is shown in Table 4.

Comparative Example 4

The same procedure as in Example 13 was repeated except for using 5% by mass (on the basis of the raw amide) of the catalyst obtained in Comparative Production Example 1 in place of 5% by mass (on the basis of the raw amide) of the catalyst obtained in Production Example 2 upon conducting the reaction. The composition of the final reaction product is shown in Table 4.

TABLE 4

|  | Catalyst | Reaction Pressure (MPa) | Composition of reaction product (mass %) | | | |
|---|---|---|---|---|---|---|
|  |  |  | DMLA*[1] | DLMA*[2] | LA*[3] | others |
| Example 13 | Production Example 2 | 8 | 88.4 | 5.1 | 5.2 | 1.3 |
|  |  | 2 | 86.6 | 5.4 | 6.8 | 1.2 |
|  |  | 0.5 | 84.9 | 5.2 | 8.3 | 1.6 |
|  |  | 0.2 | 81.1 | 10.5 | 5.7 | 2.7 |
| Comparative Example 4 | Comparative Production Example 1 | 8 | 65.1 | 18.4 | 8.8 | 7.7 |
|  |  | 2 | 65.4 | 21.9 | 6.1 | 6.6 |
|  |  | 0.5 | 67.1 | 21.2 | 5.8 | 5.9 |
|  |  | 0.2 | 53.7 | 34.6 | 2.2 | 9.5 |

Note
*[1]DMLA = Dimethyl lauryl amine;
*[2]DLMA = Dilauryl monomethyl amine; ;
*[3]LA = Lauryl alcohol Example 14

A rotary autoclave was charged with 300 g of N,N-dimethyl stearyl amide and 5% by mass of the catalyst produced in Production Example 1 (on the basis of the raw amide). An inside of the autoclave was purged with nitrogen, and then hydrogen was introduced thereinto until an inside pressure of the autoclave was increased to 1.5 MPa. Thereafter, while maintaining the inside pressure of the autoclave at 1.5 MPa, hydrogen was introduced into the reaction system at a rate of 40 L/h (1.35 mol/h per 1 mol of the raw amide). Next, the reaction system was heated to 250° C. at which the respective components were reacted with each other, and the reaction product was sampled when the amount of the raw amide was reduced to 1%. The thus sampled reaction product was subjected to filtration to remove the catalyst therefrom, and then the composition of the thus separated reaction solution was analyzed by gas chromatography. As a result, it was confirmed that the final reaction product was composed of 70.0% by mass of N,N-dimethyl stearyl amine, 7.0% by mass of N,N-distearyl methyl amine and 5.6% by mass of stearyl alcohol.

Example 15

The reaction product obtained in Example 1 was subjected to purification and fractionation procedure by distillation, thereby obtaining lauryl dimethyl amine (purity as measured by gas chromatography: 99.9%). A 1 L four-necked flask equipped with a thermometer, a stirrer, a cooling tube and a dropping funnel was charged with 258.8 g of the thus obtained lauryl dimethyl amine (weight-average molecular weight: 215.7) and 439.8 g of ion-exchanged water, and the contents of the flask were heated to 90° C. Thereafter, 91.9 g of a 45% hydrogen peroxide aqueous solution was dropped into the flask over 1 h. Further, the contents of the flask were stirred at 90° C. for 8 h, thereby obtaining a reaction product containing about 35% of lauryl dimethyl amine oxide. The hue and odor of the thus obtained product were evaluated immediately after production thereof and after preserving the product at 60° C. The results are shown in Table 5.

Examples 16 and 17

The same procedure as in Example 15 was repeated except for using the reaction products respectively obtained in Examples 4 and 8 in place of the reaction product obtained in Example 1, thereby respectively obtaining reaction products containing lauryl dimethyl amine oxide. The hue and odor of the thus obtained products were evaluated immediately after production thereof and after preserving the products at 60° C. The results are shown in Table 5.

Comparative Example 5

The same procedure as in Example 15 was repeated except for using the reaction product obtained in Comparative Example 1 in place of the reaction product obtained in Example 1, thereby obtaining a reaction product containing lauryl dimethyl amine oxide as aimed. The hue and odor of the thus obtained product were evaluated immediately after production thereof and after preserving the product at 60° C. The results are shown in Table 5.

Meanwhile, the hue and odor of the respective reaction products were evaluated by the following methods.

(Evaluation of Hue)
The sample was placed in a glass container for measurement to measure a hue thereof using a tintometer "Lovibond Tintometer PFX995".

(Evaluation of Odor)
The sample was subjected to sensory test by expert panelists to evaluate an odor thereof according to the following 4 ratings ⊚, ○, Δ and x.

Evaluation Criteria
⊚: Excellent
○: Good
Δ: Slightly poor
x: Poor

TABLE 5

|  | Amine product | Hue (APHA) | | | Odor | |
|---|---|---|---|---|---|---|
|  |  | IA*[1] | After 3 days | After 6 days | IA*[1] | After 3 days |
| Example 15 | Example 1 | 5 | 30 | 250 to 300 | ○ | ○ |
| Example 16 | Example 4 | 10 | 40 | 300 to 500 | ○ | ○ |
| Example 17 | Example 8 | 5 | 30 | 300 to 400 | ○ | ○ |
| Comp. Example 5 | Comp. Example 1 | 10 | 50 | 500< | ○ | Δ |

Note
*[1]IA = Immediately after production

INDUSTRIAL APPLICABILITY

In the process for producing the tertiary amine according to the present invention, the high-purity aliphatic tertiary amine containing a less amount of by-products can be produced. The aliphatic tertiary amine produced according to the process of the present invention is an important intermediate product in domestic and industrial application fields, and can be used in extensive applications such as, for example, fabric softeners for fiber products, antistatic agents, additives for gasoline, shampoos, rinses, bactericides and detergents.

The invention claimed is:

1. A process for producing a tertiary amine represented by the following general formula (2):

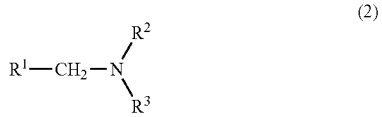

(2)

wherein $R^1$ is a linear or branched, saturated or unsaturated aliphatic hydrocarbon group having 1 to 23 carbon atoms; and $R^2$ and $R^3$ are each independently a linear or branched alkyl group having 1 to 6 carbon atoms, said process comprising the step of subjecting an amide represented by the following general formula (1):

(1)

wherein $R^1$, $R^2$ and $R^3$ are the same as defined above, to hydrogenation reduction in the presence of a catalyst consisting of copper, at least one element selected from the group consisting of elements belonging to Groups 2, 3 and 7 of the Periodic Table (long form of the periodic table), and optionally at least one element selected from the group consisting of elements belonging to Groups 8 to 10 of the Periodic Table.

2. The process according to claim 1, wherein the at least one element selected from the group consisting of elements belonging to Groups 2, 3 and 7 of the Periodic Table is at least one element selected from the group consisting of calcium, barium, manganese and lanthanum.

3. The process according to claim 1, wherein the catalyst further contains at least one element selected from the group consisting of elements belonging to Groups 8 to 10 of the Periodic Table.

4. The process according to claim 3, wherein the at least one element selected from the group consisting of elements belonging to Groups 8 to 10 of the Periodic Table is at least one element selected from the group consisting of platinum-group elements.

5. The process according to claim 1, wherein a mass ratio of the at least one element selected from the group consisting of elements belonging to Groups 2, 3 and 7 of the Periodic Table to the copper (at least one element selected from the group consisting of elements belonging to Groups 2, 3 and 7 of the Periodic Table/copper) in the catalyst is from 0.05 to 10.

6. The process according to claim 1, wherein the catalyst is used in an amount of from 0.05 to 20% by mass on the basis of the amide represented by the general formula (1).

7. A process for producing an amine oxide, comprising the step of reacting the tertiary amine obtained by the process as defined in claim 1 with hydrogen peroxide.

8. The process according to claim 3, wherein the at least one element selected from the group consisting of elements belonging to Groups 2, 3 and 7 of the Periodic Table is at least one element selected from the group consisting of calcium, barium, manganese and lanthanum.

9. The process according to claim 3, wherein a mass ratio of the at least one element selected from the group consisting of elements belonging to Groups 2, 3 and 7 of the Periodic Table to the copper (at least one element selected from the group consisting of elements belonging to Groups 2, 3 and 7 of the Periodic Table/copper) in the catalyst is from 0.05 to 10.

10. The process according to claim 3, wherein the catalyst is used in an amount of from 0.05 to 20% by mass on the basis of the amide represented by the general formula (1).

* * * * *